United States Patent
Chukoskie et al.

(10) Patent No.: US 12,212,813 B2
(45) Date of Patent: Jan. 28, 2025

(54) SYSTEMS AND METHODS FOR CHARACTERIZING JOINT ATTENTION DURING REAL WORLD INTERACTION

(71) Applicant: THE REGENTS OF THE UNIVERSITY OF CALIFORNIA, Oakland, CA (US)

(72) Inventors: Leanne Chukoskie, San Diego, CA (US); Pamela Cosman, La Jolla, CA (US); Pranav Venuprasad, Framingham, MA (US); Anurag Paul, Sunnyvale, CA (US); Tushar Dobhal, Bentonville, AR (US); Tu Nguyen, Tay Ninh Province (VN); Andrew Gilman, Tauranga (NZ)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 202 days.

(21) Appl. No.: 17/620,082

(22) PCT Filed: Jun. 25, 2020

(86) PCT No.: PCT/US2020/039536
§ 371 (c)(1),
(2) Date: Dec. 16, 2021

(87) PCT Pub. No.: WO2020/264101
PCT Pub. Date: Dec. 30, 2020

(65) Prior Publication Data
US 2022/0360847 A1    Nov. 10, 2022

Related U.S. Application Data

(60) Provisional application No. 62/866,573, filed on Jun. 25, 2019.

(51) Int. Cl.
*H04N 21/442*    (2011.01)
*G06F 3/01*    (2006.01)

(52) U.S. Cl.
CPC ....... *H04N 21/44218* (2013.01); *G06F 3/013* (2013.01)

(58) Field of Classification Search
CPC ..... H04N 21/44218; G06F 3/013; A61B 5/16; A61B 5/163; A61B 5/725; A61B 3/113
(Continued)

(56) References Cited

U.S. PATENT DOCUMENTS

2002/0115925 A1* 8/2002 Avrin ............... A61B 5/242
                                                    600/407
2005/0004496 A1* 1/2005 Pilu ................. H04N 23/61
                                                    600/595

(Continued)

OTHER PUBLICATIONS

International Search Report and Written Opinion mailed Sep. 4, 2020 for International Application No. PCT/US2020/039536.

(Continued)

*Primary Examiner* — Adil Ocak
(74) *Attorney, Agent, or Firm* — Sheppard, Mullin, Richter & Hampton LLP

(57) ABSTRACT

Systems, devices, and methods are disclosed for characterizing joint attention. A method includes dynamically obtaining video streams of participants; dynamically obtaining gaze streams; dynamically providing a cue to the participants to view the object; dynamically detecting a joint gaze based on the gaze streams focusing on the object over a time interval; and dynamically providing feedback based on detecting the joint gaze.

17 Claims, 12 Drawing Sheets

(58) Field of Classification Search
USPC .......................................................... 725/12
See application file for complete search history.

(56) References Cited

U.S. PATENT DOCUMENTS

| | | | | |
|---|---|---|---|---|
| 2006/0262140 | A1* | 11/2006 | Kujawa | B60K 35/28 |
| | | | | 345/633 |
| 2013/0278631 | A1 | 10/2013 | Border et al. | |
| 2014/0361971 | A1* | 12/2014 | Sala | G06F 3/013 |
| | | | | 345/156 |
| 2015/0268821 | A1* | 9/2015 | Ramsby | G06V 40/19 |
| | | | | 715/765 |
| 2016/0262613 | A1* | 9/2016 | Klin | A61B 3/0025 |
| 2017/0004573 | A1* | 1/2017 | Hussain | G06Q 20/40 |
| 2017/0061034 | A1 | 3/2017 | Ritchey et al. | |
| 2018/0088340 | A1* | 3/2018 | Amayeh | G06V 20/64 |
| 2018/0239523 | A1* | 8/2018 | Rosenberg | G06F 3/04842 |
| 2020/0097076 | A1* | 3/2020 | Alcaide | G06F 3/012 |

OTHER PUBLICATIONS

International Preliminary Report on Patentability dated May 21, 2021 for International Application No. PCT/US2020/039536.

* cited by examiner

SYSTEMS AND METHODS FOR CHARACTERIZING JOINT ATTENTION DURING REAL WORLD INTERACTION

CROSS-REFERENCE TO RELATED APPLICATIONS

The present application is a U.S. national phase of PCT International Patent Application No. PCT/US2020/039536, filed Jun. 25, 2020 and titled "SYSTEMS AND METHODS FOR CHARACTERIZING JOINT ATTENTION DURING REAL WORLD INTERACTION", which claims priority to U.S. Patent Application No. 62/866,573, filed Jun. 25, 2019 and titled "SYSTEMS AND METHODS FOR CHARACTERIZING JOINT ATTENTION DURING REAL WORLD INTERACTION," which is incorporated herein by reference in its entirety.

STATEMENT REGARDING FEDERALLY SPONSORED R&D

This invention was made with U.S. government support under Grant No. SMA1640909 awarded by National Science Foundation. The U.S. government has certain rights in the Invention.

TECHNICAL FIELD

Various embodiments generally relate to gaze assessment. More particularly, various embodiments are related to gaze assessment of multiple subjects.

BRIEF SUMMARY OF EMBODIMENTS

Embodiments of the disclosure are directed to methods, systems, and devices for detecting joint gaze. In embodiments, a computer-implemented method for assessing joint gaze may include a number of operations. One operation may include dynamically obtaining video streams of participants. The video streams may include videos of a real-world environment from each of the participants' perspective. At least one frame from each of the video streams may include an object. One operation may include dynamically obtaining gaze streams. A given gaze stream may include gaze location data for a given participant., The gaze location data identifies where the given participant is looking in the real-world environment as a function of time. One operation may include dynamically providing a cue to the participants to view the object. One operation may include dynamically detecting a joint gaze based on the gaze streams focusing on the object over a time interval. One operation may include dynamically providing feedback based on detecting the joint gaze.

In embodiments, the given gaze stream may include a gaze confidence score specifying an accuracy of the gaze location data.

In embodiments, another operation may include dynamically filtering the gaze location data based on a Kalman filter and the gaze confidence score.

In embodiments, another operation may include generating a visualization of a bounding box surrounding the object. One operation may include dynamically displaying the visualization when the object is in a current frame of a given video stream.

In embodiments, another operation may include dynamically detecting the object in a current frame of a given video stream using a convolutional neural network. One operation may include generating a visualization of a bounding box surrounding the object in the current frame. One operation may include dynamically displaying the visualization when the object is in the current frame.

In embodiments, the cue may include one of an audio cue and a visual cue.

In embodiments, the feedback may include one of an audio cue and a visual cue.

In accordance with additional aspects of the present disclosure, a system for analyzing behavior of a human subject may include a processor and a non-transitory storage medium coupled to the processor to store instructions, which when executed by the processor, cause the processor to perform a number of operations. One operation may include dynamically obtaining video streams of the participants. The video streams may include videos of a real-world environment from the participants' perspective. At least one frame of the video streams may include an object. One operation may include dynamically obtaining gaze streams occurring simultaneously with the video streams. A given gaze stream may include gaze location data for a given participant. The gaze location data identifies where the given participant is looking in the real-world environment as a function of time. One operation may include dynamically providing a cue to the participants to view the object. One operation may include dynamically detecting a joint gaze based on the gaze streams focusing on the object over a sequence of time points. One operation may include dynamically providing feedback based on detecting the joint gaze.

In embodiments, the given gaze stream further may include a gaze confidence score specifying an accuracy of the gaze location data.

In embodiments, another operation may include dynamically filtering the gaze location data based on a Kalman filter and the gaze confidence score.

In embodiments, another operation may include generating a visualization of a bounding box surrounding the object. One operation may include dynamically displaying the visualization when the object is in a current frame of a given video stream.

In embodiments, another operation may include dynamically detecting the object in a current frame of a given video stream using a convolutional neural network. One operation may include generating a visualization of a bounding box surrounding the object in the current frame. One operation may include dynamically displaying the visualization when the object is in the current frame.

In embodiments, another operation may include dynamically detecting a gaze triad from at least one participant. A gaze triad may include a look to a face before and after a look to the object.

In embodiments, dynamically detecting a joint gaze may include dynamically applying a runlength filter. The runlength filter may include a window size parameter specifying a number of frames to consider together and a hit threshold specifying a minimum number of hits in the number of frames to be identified as a gaze.

In accordance with additional aspects of the present disclosure, a computer-implemented method for detecting joint gazes may be implemented in a computer system. The computer system may include a processor, a first set of cameras to capture video streams of a real-world environment, a second set of cameras to capture gaze streams of participants' eyes, non-transitory storage medium, and see-through displays. The computer-implemented method may include a number of operations. One operation may include dynamically obtaining the video streams of the participants.

At least one frame from each of the video streams may include an object. One operation may include dynamically obtaining gaze streams occurring simultaneously with the video streams. A given gaze stream may include gaze location data for a given participant. The gaze location data identifies where the given participant is looking in the real-world environment as a function of time. One operation may include generating a bounding box surrounding the object. One operation may include dynamically displaying the bounding box when the object is in a current frame of a given video stream. One operation may include dynamically detecting a joint gaze based on the gaze streams focusing on the object over a time interval. One operation may include dynamically providing feedback based on detecting the joint gaze.

In embodiments, the given gaze stream may include a gaze confidence score specifying an accuracy of the gaze location data.

In embodiments, generating the bounding box surrounding the object may include a number of operations. One operation may include dynamically detecting the object in a current frame of the given video stream using a convolutional neural network. One operation may include generating a visualization of a bounding box surrounding the object in the current frame.

In embodiments, generating the bounding box surrounding the object may include dynamically changing a size of the bounding box based on one of a current size of the bounding box, a gaze confidence score, and a depth of the object from the given participant.

In embodiments, another operation may include dynamically detecting a gaze triad. A gaze triad may include a look to a face before and after a look to the object.

In embodiments, dynamically detecting a joint gaze may include dynamically applying a runlength filter. The runlength filter may include a window size parameter specifying a number of frames to consider together and a hit threshold specifying a minimum number of hits in the number of frames to be identified as a look.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

Figure 1:
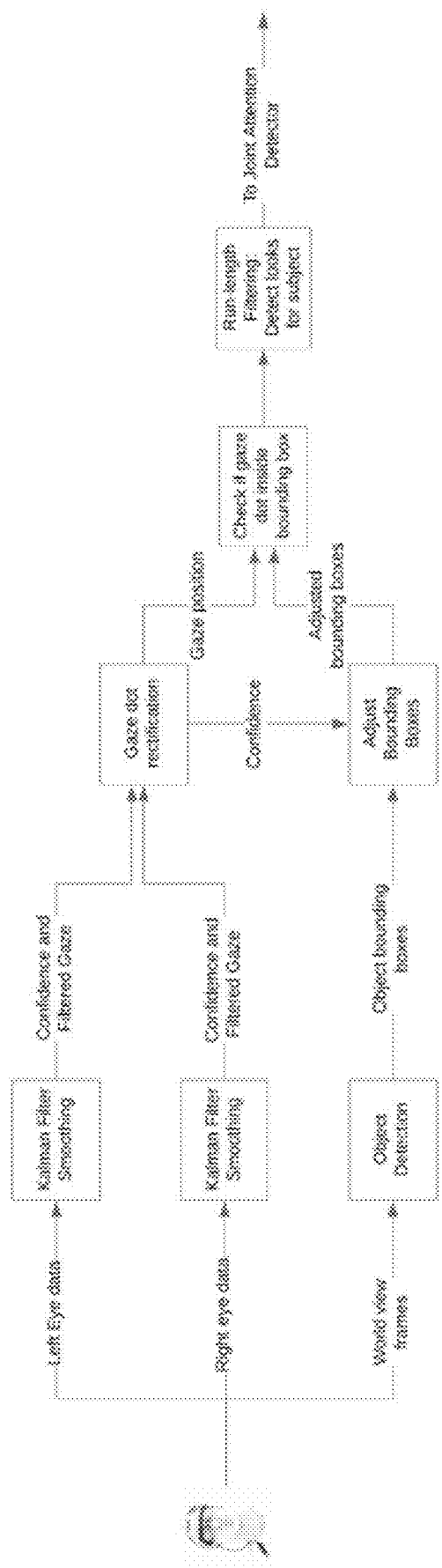
FIG. 1 is an operational flow diagram illustrating an example process for characterizing joint attention, in accordance with various embodiments of the present disclosure.

Joint attention is an essential part of the development process of children, and impairments in joint attention are considered as the first symptoms of autism. Joint attention is a crucial skill that most children learn in their first year of life. By sharing gaze on an object with a caregiver, and looking between the object and the caregiver, children learn names of items, rules about object use, and motor behaviors, all of which are used for later developmental skills. Nature provides a wide array of cues and experiences that are enough to help most children develop along a relatively predictable, albeit complex path. For children with neurological differences, however, these cues may not be adequate and their experiences may be a typical enough that the child does not experience the learning benefits enjoyed by their typical peers. Joint attention skill does not come easily to some children, including children with autism spectrum disorders (ASD), and this foundational deficit can also lead to functional difficulties in social situations, as well as other domains. Successful joint attention skill requires the marshaling of visual attention and gaze in a fast and accurate manner. However, fast shifts of visual attention and accurate shifts of gaze may be deficient in individuals with ASD. In fact, disordered visual orienting is among the earliest signs of ASD identified in prospective studies of infant siblings.

Clinical psychologists have created intensive behavioral interventions for improving joint attention, involving many hours per week of therapy from a professional with training in this specific behavioral intervention. These individuals are rare and their limited time also limits the availability of these important interventions. To continue the valuable intervention in the absence of professionals, parents should be independently trained to deliver the therapy—which can be difficult especially in children who frequently show a greater interest in orienting to objects than to people.

The presently disclosed technology may be used to characterize joint attention in real time, by studying the interaction of two subjects (e.g., people) with each other and with multiple objects present in the room. This may be done by capturing the subjects' gaze through eye-tracking glasses and detecting their looks on predefined indicator objects. A deep learning network may be trained and deployed to detect the objects in the subjects' field of vision by processing the video feed of the world-view-camera mounted on the eye-tracking glasses. The subjects' look patterns may be determined and a real-time audio response may be provided when a joint attention is detected, i.e. when their looks coincide. The presently disclosed technology may include filtering and thresholding techniques.

The presently disclosed technology discloses a real-time joint attention detection system that efficiently coordinates between data of two or more eye-tracking glasses and provides feedback when a joint look may be detected. The presently disclosed technology can provide a different kind of feedback for a child that may be for whatever reason-not responding well to the usual cues in the environment that children typically use to learn where and when to look. The presently disclosed technology may be relatively low cost and can be used by parents and caregivers in their homes as often as may be convenient. This removes the barriers of time and place that are often created by the standard nature of clinical care.

An example system may include pairs of gaze-tracking glasses (e.g., one for the child, one for the caregiver) that can synchronize their data streams as a function of time. Augmented reality (AR) technology may be used to tag object surfaces, such that simultaneous looks to each object surface may trigger an action, such as a sound. In some embodiments, individual looks by each subject may trigger a different action. By bringing together this combination of technologies, the power of gaze-contingent video games used in co-pending applications can be brought out of the computer and into the real world to facilitate interaction and learning between a caregiver and a young child with ASD.

The gaze-tracking glasses may include one or more red-green-blue (RGB) cameras, one or more infrared cameras, and other sensors. For example, the one or more RGB cameras may be capable of producing 720×1280 frames at about 30 frames per second (fps). The one or more RGB cameras may be located above the eyebrows on the glasses' frame. Continuing to describe an example pair of gaze-tracking glasses, the one or more infrared cameras may be capable of about 120 fps pupil tracking. The one or more infrared cameras may be positioned below each eye on the surface of the glasses closest to the eye. This example binocular eye setup may output the gaze location data and a confidence score, which may be a measure of the accuracy of the gaze location in the world-view frame.

The presently disclosed technology may integrate face identification, as well as facial recognition in real time, so in addition to objects, children can also be rewarded for looks to faces. The presently disclosed technology may signal individual and joint gaze to tagged objects quickly and accurately. Additionally, the glasses system may be designed to be both comfortable for the child to wear and easy to use for the caregiver.

FIG. 1 is an operational flow diagram illustrating an example process for characterizing joint attention, in accordance with various embodiments of the present disclosure. The data produced by the glasses may be received by the one or more listeners running on the system. The listeners may be asynchronous message listeners. The listeners may receive the gaze positions and confidence scores for each eye from the eye cameras (e.g., infrared camera) and the world-view frames from the world-view camera (e.g., RGB camera). The gaze position data from each eye may be smoothed using one or more filters. For example, a Kalman filter may be used, and the corresponding confidence scores may be used to obtain a single rectified gaze stream. An object detector, as will be described herein, may input the world-view frames and may output the bounding boxes describing the location of the objects present in the frames. These bounding boxes may be adjusted using the obtained gaze confidence score to account for any inaccuracies involved in the measurements. Given that the frame rate of the eye cameras may be four times that of the world-view camera, the data may be processed at this point when a new world-view frame may be received. This may reduce the number of computations for real-time usage without impacting the overall detection accuracy. For each obtained bounding box, it may be determined whether a gaze dot is inside the bounding box, to obtain a Boolean decision. The series of decision outputs may be filtered using a Runlength algorithm which defines and detects "looks" on each object, as will be described herein. It should be appreciated that other filters may be used to detect the looks or otherwise filter the data generated by the eye cameras and the world-view camera. This "look" data from both the glasses may be passed to the Joint-Attention detector which may provide an audio feedback, or other feedback, when a "joint look" is successfully detected. In some embodiments, checking whether a gaze dot is inside the bounding box and applying runlength filtering may be combined into a more general signal processing approach. This approach may include using both the gaze dot position and the bounding box information over a sequence of time points to determine whether or not there is a look to an object. This approach may leverage information related to how far the gaze dot is outside a bounding box, if outside the bounding box, information related to how close the gaze dot is to the center of the bounding box, if it is inside the bounding box, the rate at which the gaze dot is moving, and other information. For example, this may include using conditional random fields, thought it should be appreciated that other techniques may be used. The time points for the gaze dot position and the time points for the bounding boxes may not be the same time points. For example, with one example pair of glasses, the gaze dot position may be obtained at a faster rate than the video frames may be obtained.

In one embodiment, object detection in the world-view of the subjects may be based off a compact version of the YOLOv3 network (e.g., YOLOv3-tiny). It should be appreciated that other Convolutional Neural Network-based approaches for object detection may be used for detection accuracy (e.g., Faster R-CNN, R-FCNNs, etc.). In embodiments, the objection detection approach may include Tiny Darknet, a small Darknet model which has about 23 layers as opposed to other networks which may have more than about 100 layers.

Figure 2:
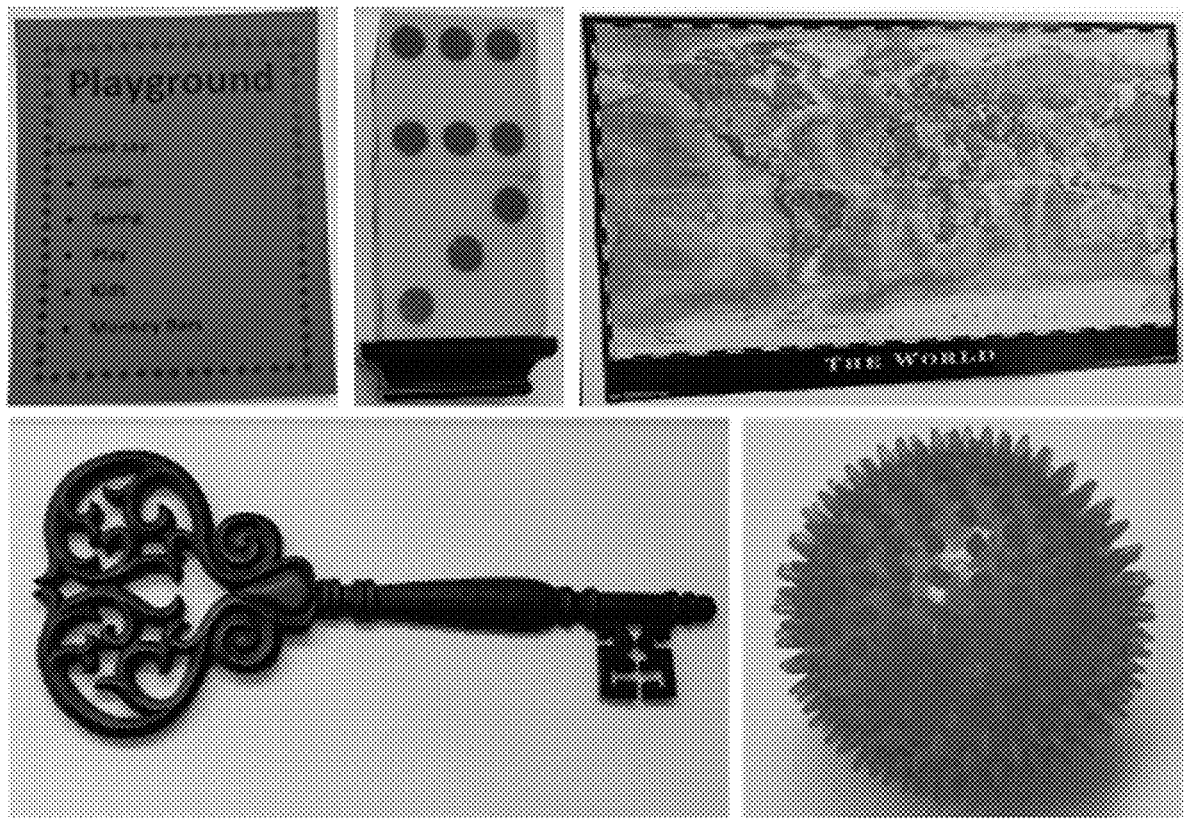
FIG. 2 illustrates example objects in an example environment, in accordance with various embodiments of the present disclosure.

FIG. 2 illustrates example objects in an example environment, in accordance with various embodiments of the present disclosure. As illustrated, the five objects include a yellow and red dice, black key, red taboo card, green spiky ball, and map. In this example, the object detection approach may have been trained based on these five objects. Of these objects, the dice, key, and map may be placed on a wall approximately eight feet away from the subjects, and the ball and the card may be kept on a table in front of the participants. Training images of the five objects may be collected from the world-view camera with different subjects wearing the glasses. In total, there were approximately 100,000 training images. Table 1 shows the split of instances of the objects in the training images.

TABLE 1

Number of instances of each object in the training set

|  | Ball | Dice | Key | Map | Cards |
|---|---|---|---|---|---|
| Number of Frames | 51798 | 39835 | 42102 | 30195 | 30248 |
| Approx. Time (min) | 14 | 11 | 11 | 8 | 8 |

Figure 3:
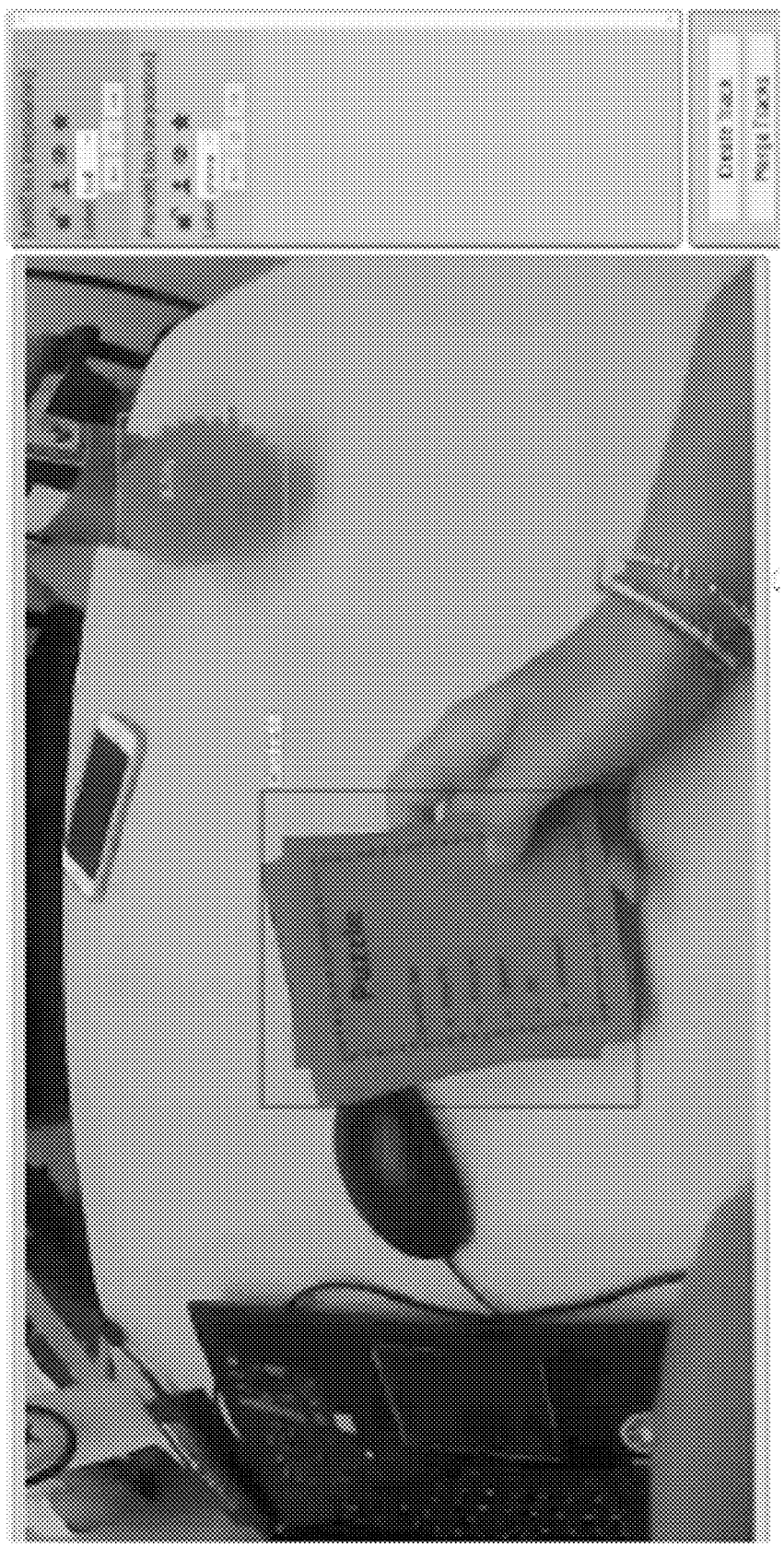
FIG. 3 illustrates example bounding boxes to identify objects in an environment, in accordance with various embodiments of the present disclosure.

FIG. 3 illustrates example bounding boxes to identify objects in an environment, in accordance with various embodiments of the present disclosure. As illustrated, a minimum enclosing rectangle was manually placed around each object to serve as the ground truth (GT) during training with the help of Computer Vision Annotation Tool (CVAT). Both the taboo card and the ball are in the real-world frame and have bounding boxes around the objects. It should be appreciated that other tools may be used to apply bounding boxes to various objects. In this example, a bounding box was applied around an object if at least about 50% of the object was present in the world-view frame, according to visual inspection. It should be appreciated that different percentages may be appropriate for different applications (e.g., 10%, 25%, 30%, 40%, 70%, etc.). The CVAT tool may include an interpolation feature, which it uses to generate bounding boxes across adjacent frames. The interpolation feature may help reduce the time and processing required to ground truth the videos. In embodiments, one or more of object detection, pattern recognition, and edge detection may be used to detect and apply bounding boxes to the objects.

For training the object detector, pre-trained weights may be used. An example training dataset may include the COCO dataset. The model may have been trained for about 150,000 iterations with a learning rate of about 0.001 and momentum of about 0.9. The performance was evaluated by computing: (1) Intersection over Union (IoU) between the bounding boxes obtained from manual annotation and the detection network, (2) True Positive Rate (TPR) which represents the fraction of the ground truth boxes detected by the network with a non-zero IoU, and (3) Precision which represents the percentage of correct detections with respect to the total number of detections.

As discussed before, each pair of glasses may provide two data streams—one of the world-view and one of gaze data collected from tracking the two pupils. The gaze data stream may provide the coordinates of the gaze dot in the world-view image and a corresponding confidence with this coordinate. In embodiments, Kalman filtering may be applied to the gaze data stream to correct for jitter in the gaze location. In some embodiments, expansion of the bounding box of detected objects may be applied based on the confidence of the gaze data to account for the inaccuracy in the gaze detection.

The Kalman filter may be an efficient recursive algorithm for estimating the state of a system. As used in the presently disclosed technology, the Kalman filter may be initialized with an 8-dimensional state vector and a two dimensional measurement update. Gaze dot coordinates from the glasses received at a rate of about 120 fps may serve as the measurement update. A variable velocity and acceleration model may be used with the Kalman filter where the initial noise and delta time estimates may be obtained empirically.

In some embodiments, an algorithm for removing the noise introduced due to blinking may be included to process the data. Using a threshold value, noisy measurements due to blinking can be identified and removed from the data stream before being sent to the Kalman filter.

Figure 4A:
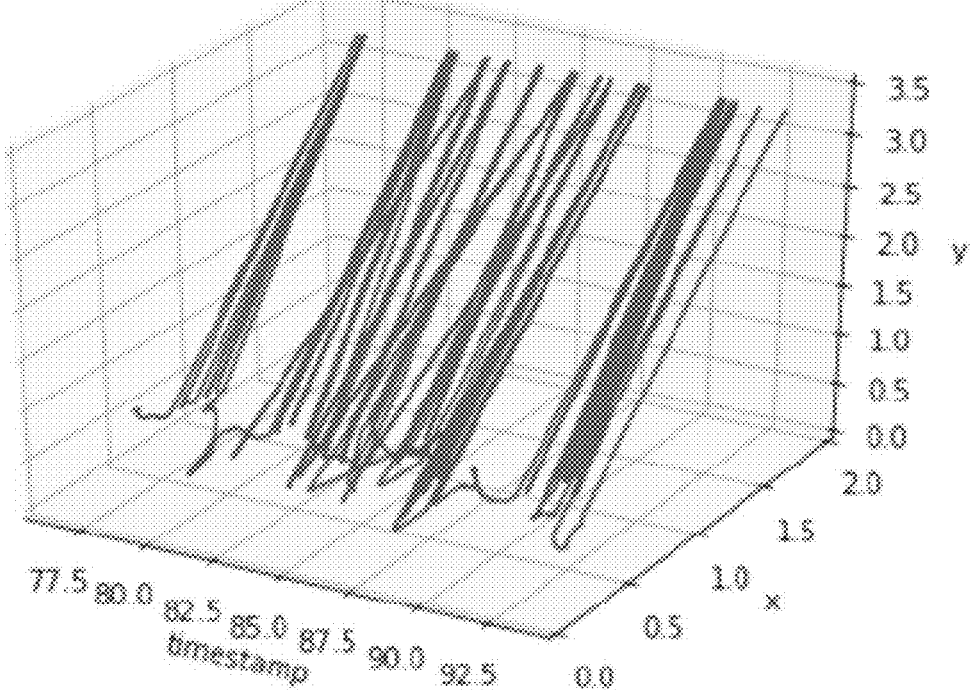
FIG. 4A illustrates a graph of example gaze data, in accordance with one embodiment of the present disclosure.

FIG. 4A illustrates a graph of example gaze data, in accordance with one embodiment of the present disclosure. As illustrated, the values jump back and forth between about (0.5, 0.5) and about (2.0, 3.0) without any filtering.

Figure 4B:
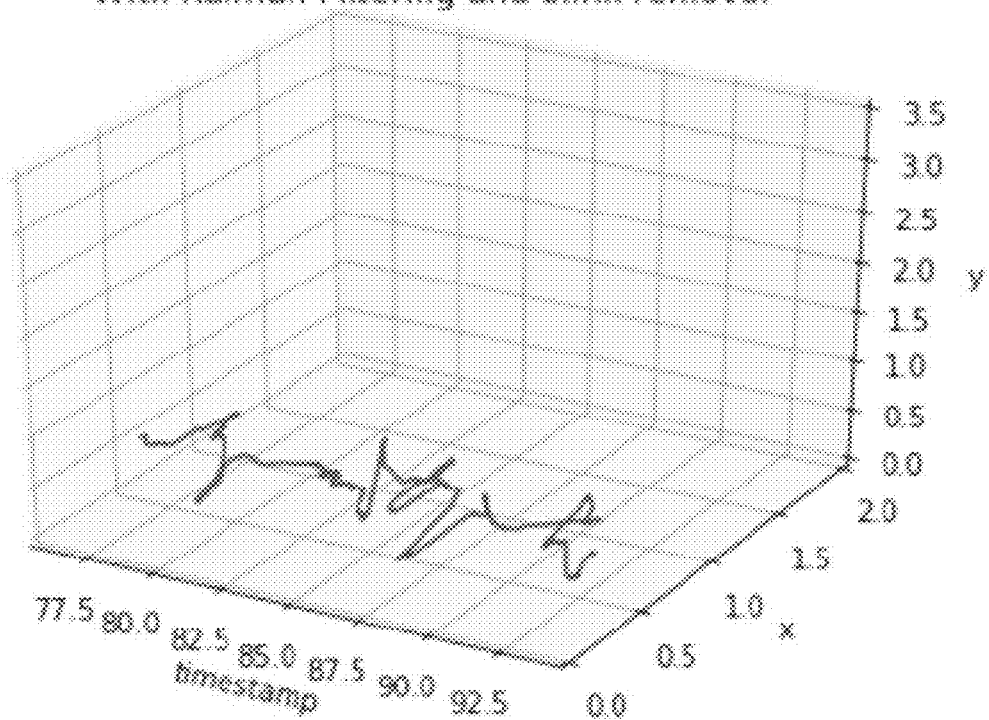
FIG. 4B illustrates a graph of example gaze data that has been filtered, in accordance with one embodiment of the present disclosure.

FIG. 4B illustrates a graph of example gaze data that has been filtered, in accordance with one embodiment of the present disclosure. As illustrated, the values are much more consistent with the Kalman filtering and the blink filtering.

In embodiments, the gaze confidence score may be utilized to rectify the gaze stream and to ensure improved tracking results. For example, if the one or more infrared cameras detect the person's gaze with a confidence greater than a threshold of about 0.8, the mean may be computed, otherwise, the data of the one with a higher gaze confidence was used. It should be appreciated that the threshold value may be less (e.g., 0.5, 0.6, 0.75, etc.).

In embodiments, bounding boxes around the various objects used in the experiment were expanded proportional to the depth of the object in the world-view and based inversely on the confidence of the gaze dot location. The bounding boxes may be expanded because, in some cases, even when the subject may be looking at an object, their gaze dot could be just outside the bounding box for that object, possibly due to one or more of poor calibration, poor sensor data, or gaze drift. In order to proportionally expand the bounding boxes, w may represent the width, and h may represent the height of the bounding box as provided by the object detection system. c may represent the confidence provided by the system regarding a gaze dot position, and a(x) may represent the correction based on depth x of the object. The expanded width and height of the object, I, may be $$w = w + \{(1-c)*a(x_i)\} \quad (1)$$

$$h = h + \{(1-c)*a(x_i)\} \quad (2)$$

Continuing the example above, two depths are considered: approximately 8 feet for the objects which are on the wall (e.g., key, dice, and map) and 1.5 feet for the objects which are on the table (e.g., ball, card). The corresponding values of a(x) are 30 pixels for x=8 ft and 15 pixels for x=1.5 ft. This adjustment may expand the bounding box when the glasses provide low confidence on the gaze location and may expand for objects that are farther away.

As described above, the object detection system may provide bounding boxes for the objects detected in a particular frame for the world-view of the subjects. These bounding boxes may be expanded based on the confidence of the gaze dot location. For each subject, if the gaze dot is within the bounding box of an object, it may be deemed a 'hit' for the object, else it may be deemed a 'miss.' A look may be an inspection typically involving an aggregated series of fixations and small re-orienting saccades or microsaccades. A saccade may refer to a re-orienting movement which may be interposed in steady intervals of fixations which characterize human gaze behavior. A typical look for examining an object can last from about 100 to about 200 ms to about a number of seconds. In embodiments, the onset of a look may be used to declare with reasonable certainty that both subjects are looking at the same object.

Runlength filtering with parameters W and O may be applied to the data stream of hits and misses to determine a look for each subject. W may represent the window size or the number of frames that should be considered together and O may represent the minimum number of hits in that window to declare it to be a look. For example, a run-length filter RL(1,1) with parameters W=1 and O=1 would imply that if there is just one frame of hit for an object, an onset of a look at the object may be declared. As another example, a runlength filter RL(4,3) with parameters W=4 and O=3 would require at least 3 hits in any 4 consecutive frames for it to be declared as the beginning of look. If the look for both subjects fall on the same object, then a joint look may be detected and, in one example, a beep sound may be provided to the experimenter as feedback for detecting joint attention. The joint look may occur at the same time, within the same window, or within a time threshold. The time threshold may be on the order or milliseconds, decisecond, centisecond, or seconds.

Going by the above definition, a filter with RL(1,1) may provide an earlier positive indication of joint look than would RL(4,3). Here, a first metric may be defined, Latency. Latency may represent the time it takes from the instruction to look at a particular object to detecting a joint look at that object. Using such terminology, RL(1,1) should have a lower latency than RL(4,3). Latency may include the time it takes for the two subjects to orient their gaze to the object from the instruction cue as well as the processing time for the system to detect each gaze position inside the bounding box for the appropriate runlength. Since the orienting behavior of the two subjects can be somewhat variable, for example, including a head-turn or corrective saccade in addition to the primary targeting saccade in many cases, Latency may be estimated to account for approximately 500 ms of reaction time for the two subjects. This is at least partially based on the saccadic reaction time of healthy young adults in a tightly controlled experimental setting with a visually-cued sudden-onset target may be approximately 250 ms. Accordingly, 500 ms is a conservative estimate for an orienting movement to an existing visual stimulus which may be triggered by an auditory cue, and may include a small head movement and/or a corrective saccade. It should be appreciated that the cue may also be a visual cue or a combination of cues.

The second metric, Estimated Detection Time, may be defined. Estimated Detection Time may represent the time elapsed between the estimated onset of a joint look and the instant when the system detects the joint look. As per the discussion above, Estimated Detection time can be expressed as Latency minus Estimated joint reaction time, which can be about 500 ms.

The example of RL(1,1) is merely an example, as it would be vulnerable to false positives as it could declare it to be a look if the subject was just glancing for a single frame at the object as their eyes pass over it to look at something else.

A third metric, Look Positive Predictive Value (LPPV), may be defined as follows:

$$LPPV = \frac{\text{Number of True Joint Looks Predicted}}{\text{Total Number of Joint Looks Predicted}}$$

To determine this metric, the ground truth (GT) on looks and joint looks may be defined. In some embodiments, this could be done using a manual process. In embodiments, the GT can be defined using a non-real-time process with a longer time window than may be used by the algorithms described above. For example, the GT on looks may be defined first and a GT on joint look may be obtained when the GT of looks for both subjects gives a hit. In this example, the GT algorithm for looks may find a series of four consecutive hit frames, which may be considered to be the core part of a look. The data stream may be examined both forwards and backwards in time from that core, to bridge small gaps (up to and including gaps of about length 3), to find the total extent of the look. For example, if the sequence of hits (X) and misses (0) is given as the first row below:

$$0X000XXXX00XX000000XX00$$

$$0XXXXXXXXXXXX000000XX00$$

then the core part of the look may be found starting in position 6, and the search backwards and forwards in time bridges the gaps of length 3 (to the left) and 2 (to the right) but not the gap of length 6 that occurs later in the stream. The look may be determined to have a total extent of 12 frames with an onset in position 2, as in the second row above. As illustrated, the onset of the look would be correctly found by an RL(1,1) algorithm. The runlength algorithms RL(2,2) and so on may detect looks, but may have some latency for the detected onset. On the other hand, a sequence like:

0X0000XXX000000XX000000 does not have a true look at all, and any of the RL(W,O) algorithms with W<4 and O≤w would detect a false positive. Accordingly, there may be a trade-off between latency and LPPV. It should be appreciated that different RL(W,O) algorithms may be used for different video sequences and applications.

It may be apparent from the above definition of a true look that the RL(4,4) may not have a false positive. All the other algorithms, such as RL(1,1), RL(2,2), RL(3,2), RL(4,3), and RL(3,3) may have lower latency than RL(4,4) but may have some false look detections.

In general, a metric of positive predictive value (PPV) which penalizes false positives may be used in conjunction with true positive rate (TPR) which penalizes false negatives. In embodiments, TPR for joint looks may be 1 because all true looks are eventually detected by all algorithms. It should be appreciated that TPR at the frame level for object detection may not generally be equal to unity, but TPR at the level of joint-look detection is. The relevant quantities may be LPPV and latency, where the latency metric may penalize the delay in declaring a look.

EXPERIMENTS

Calibration Routine

Initially, calibration of the glasses may be performed and may be used to map the pupil gaze location captured by the binocular eye-facing infrared cameras to the real-world frames captured by the world-view camera. The manual calibration mode may be selected in existing software and a manual marker with a bulls-eye pattern may be used. The experiment participants may be asked to keep their head still and move their eyes to look around. This method of calibration, where the wearer keeps his head still during calibration, may provide better accuracy of the gaze position than when the head may be moving around. It should be appreciated that different calibration methods may be used.

In this example calibration process, the eye cameras of the subjects may be adjusted to ensure that the pupil may be detected and tracked. Existing software may give the flexibility to adjust the intensity and minimum and maximum pupil size parameters to do this accurately. Participants may be instructed to look at the center of a marker (e.g., the bulls-eye pattern) as it moves across the wall from one extreme location to another. The bulls-eye pattern may be detected by the software in the world-view camera, which may then be correlated with the gaze position captured at that time instant, assuming that the subject was looking at the center of the pattern. A total of at least nine points may be collected, and a non-linear transformation may be used by the software to map the gaze positions to the incoming video frames. In this example, a confidence threshold of about 0.5 was used; the system may reject points which it deems to have lower accuracy than this threshold. It should be appreciated that other confidence threshold may be used (e.g., 0.1, 0.25, 0.75, 0.9, etc.). This routine may be done separately for each of the glasses as the extrema of the field of view depend greatly on the position and orientation of the participant. After the calibration, both participants may be allowed to move their heads normally and may be asked to look at the individual objects to perform a quick verbal check of the calibration routine.

Experiment Design

An example experiment may include one experimenter, who conducts the experiment, and two participants, who wear the glasses for the joint attention detection. The participants may be cued to look at the individual objects and the time taken by the pair to jointly fixate their gaze at that object may be recorded. To accurately capture the time when the instruction to look at a particular object is given, a smartphone application ("app") may be used for the experimenter to signal the participants. In an example test, eight participants were involved, and the average age was about 23. The participants were asked to switch places during the experiment. As described in an example above, the example test included five objects, with three objects placed on the wall and two objects placed on the table in front of the participants.

Figure 5:
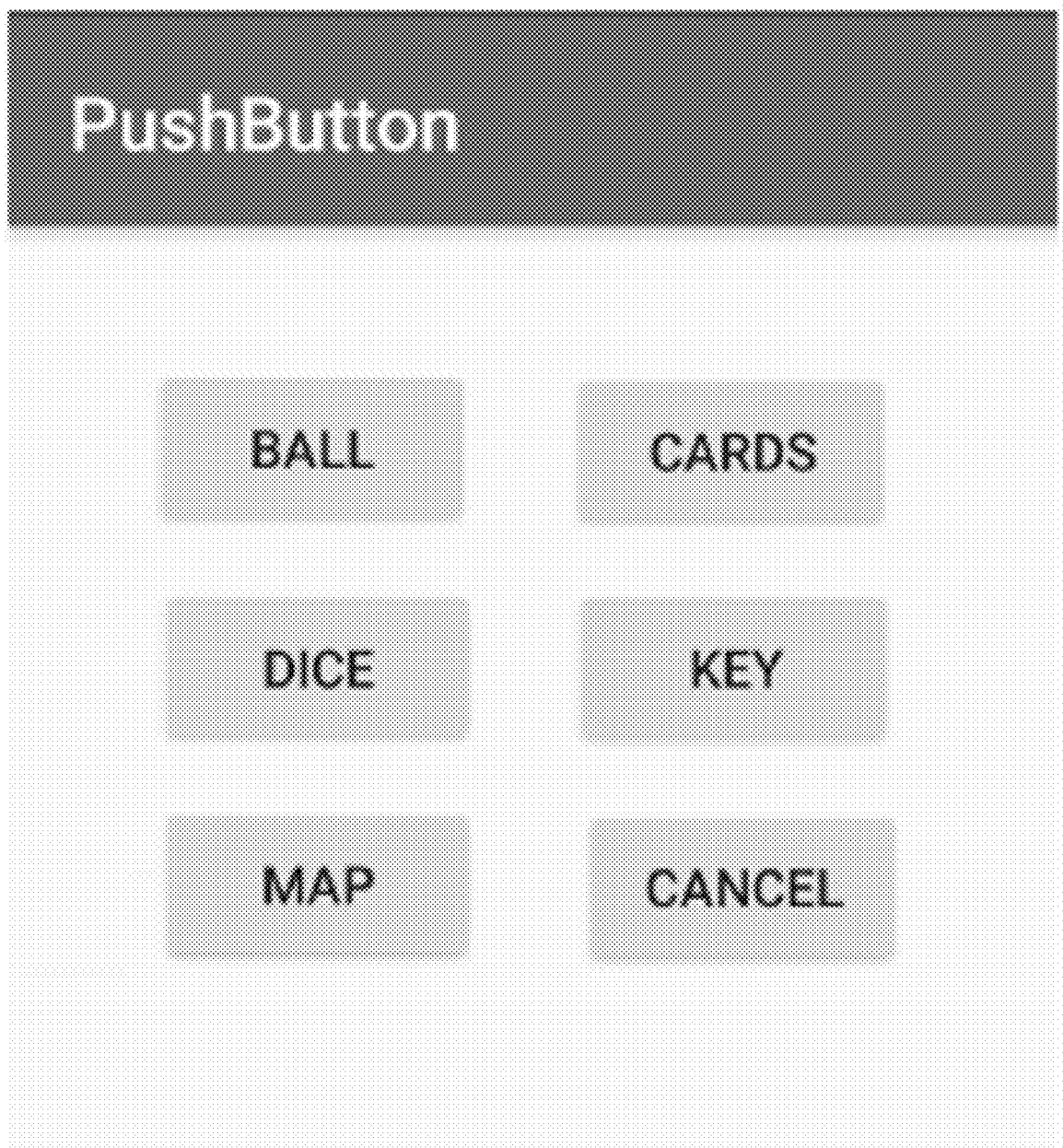
FIG. 5 illustrates an example user interface, in accordance with one embodiment of the present disclosure.

FIG. 5 illustrates an example user interface, in accordance with one embodiment of the present disclosure. As illustrated, the example user interface includes buttons of individual objects, which when pressed, or otherwise interacted with, may send a message to the server. The example user interface may be used by an experimenter. A "cancel" button, when interacted with, may discard the current reading in case of accidental clicks. The receiver server may record the timestamp when the message is received and may produce a beep, which acts as a cue for the participants to look at a specified object. In this testing, the system provided audio feedback, in real time, when the joint look on the specified object was detected. To minimize any phase difference between the recorded timestamps of the instruction to look at an object and the actual looks of the two subjects, the same hardware may be used for running the message receiver and the software. A total of five rounds were conducted, with each round constituting cues for all the five objects. Then participants are asked to switch places for another five rounds, after which the procedure may be repeated with a new pair of participants. A total of about 500 joint looks were obtained using different combinations of the participants.

Figure 6:
FIG. 6 illustrates an example world-view frame including multiple objects, in accordance with one embodiment of the present disclosure.

FIG. 6 illustrates an example world-view frame including multiple objects, in accordance with one embodiment of the present disclosure. As illustrated, the map, key, and dice are identified by the bounding boxes in the world-view frame. The gaze dot is within the bounding box of the dice.

Object Detection

In one example, the object detector was run on 80,000 test images which were manually annotated using CVAT. As described above, the performance of the detector may be evaluated by computing the IoU, TPR, and Precision. The average results for each object are summarized in Table 2.

TABLE 2

Performance of the object detector

|  | Ball | Dice | Key | Map | Cards |
| --- | --- | --- | --- | --- | --- |
| IoU | 92.3% | 92.9% | 82.1% | 86.2% | 87.5% |
| TPR | 98.9% | 99.1% | 96.8% | 94.5% | 90.3% |
| Precision | 97.0% | 97.7% | 98.2% | 96.3% | 99.3% |

Table 2 illustrates that the object detector gives an average True Positive Rate of about 95.9%. The missed cases (False negatives) may correspond to mostly edge cases, where a part of the object may be visible in the world-view frame and it has been annotated in the GT image. This may cause an error in joint attention detection if: (1) the object is visible partially, and/or (2) the wearer looks at the object out of the corner of his eyes. Since the wearer moves his head around normally, this edge case is anticipated to occur rarely and, should have negligible impact on the overall performance of the system. The network may provide a relatively lower detection rate for the cards because the portion of the cards captured by the world-view camera may be heavily dependent on its orientation with respect to the subject.

Experiment

In one example, running the software simultaneously for both glasses, the system may give a frame rate of about 16 fps. The loss of frames may be due to the two object detection networks running in parallel on the GPU. There were few readings that were discarded either because the experimenter pressed the button twice or the participants missed the audio cue provided. Apart from these scenarios, no other procedure was used for data points pre-processing.

Estimated Detection Time

The results for the Estimated Detection Time of the system with various runlength parameters for different objects may be illustrated in Table 3 and the latency may be illustrated in FIGS. 7 through 11, which will be described in further detail below. In general, the latency for each runlength parameter follows the order Map <Key <Dice <Ball <Cards. The high latency for Cards can be explained by the relatively low detection rate for cards. For the other objects, the latency for each runlength generally follows the order of decreasing object sizes. This may be because the start of a look may be detected as soon as the gaze dot falls within the object bounding boxes, which may be easier if the box size is larger. For the same object across different runlength parameters, the latency may increase from RL(1,1) to RL(4, 4).

TABLE 3

Performance of the Joint look detector: Estimated Detection Time (ms): Mean

|  | RL(1,1) | RL(2,2) | RL(3,3) | RL(3,3) | RL(4,3) | RL(4,4) |
|---|---|---|---|---|---|---|
| Ball | 373.9 | 424.5 | 465.1 | 478.6 | 517.6 | 525.6 |
| Cards | 508.6 | 571.2 | 611.0 | 659.9 | 696.8 | 714.4 |
| Dice | 333.8 | 411.6 | 446.7 | 474.0 | 507.8 | 511.1 |
| Key | 326.3 | 387.0 | 426.2 | 463.5 | 595.9 | 508.4 |
| Map | 295.1 | 349.2 | 389.0 | 403.7 | 445.5 | 451.1 |

Look Positive Predictive Value (LPPV)

The LPPV results with various runlength parameters for different objects are illustrated in Table 4 and FIGS. 7 through 11, which will be described in further detail below. A definition of a true joint look may include having a core of 4 consecutive hit frames. Accordingly, RL(4,4) has LPPV=100%. In general, as the window size parameter W increases, the LPPV also increases. This may be expected as increasing window size makes the runlength filter reach closer to the size of the core-look part of the true look and increases the possibility of detecting a true joint-look.

TABLE 4

Performance of the Joint look detector: LPPV %

|  | RL(1,1) | RL(2,2) | RL(,3) | RL(3,3) | RL(4,3) | RL(4,4) |
|---|---|---|---|---|---|---|
| Ball | 88.2 | 90.4 | 90.4 | 97.8 | 97.8 | 100.0 |
| Cards | 82.9 | 85.1 | 85.1 | 95.7 | 95.7 | 100.0 |
| Dice | 85.1 | 93.6 | 93.6 | 100.0 | 98.9 | 100.0 |
| Key | 85.1 | 90.4 | 90.4 | 98.9 | 98.9 | 100.0 |
| Map | 91.4 | 93.6 | 93.6 | 97.8 | 97.8 | 100.0 |

Across objects, LPPV generally increases with increasing bounding-box size for smaller runlength parameters. This may be due to the inherent jitter in the gaze position calculation caused by the pupil detection algorithm. As runlength filter parameters increase, the change in LPPV across objects may be almost negligible. As expected, there may be a trade-off between Latency and LPPV measurements across runlength parameters. For lower values of W and O, detection may be faster but with a lower accuracy measure. For latency sensitive applications, such as interactive AR and VR gaming, smaller runlength parameters may be suitable, whereas for use in therapeutic applications, which require higher detection accuracy, larger parameters may be preferred.

Figure 7:
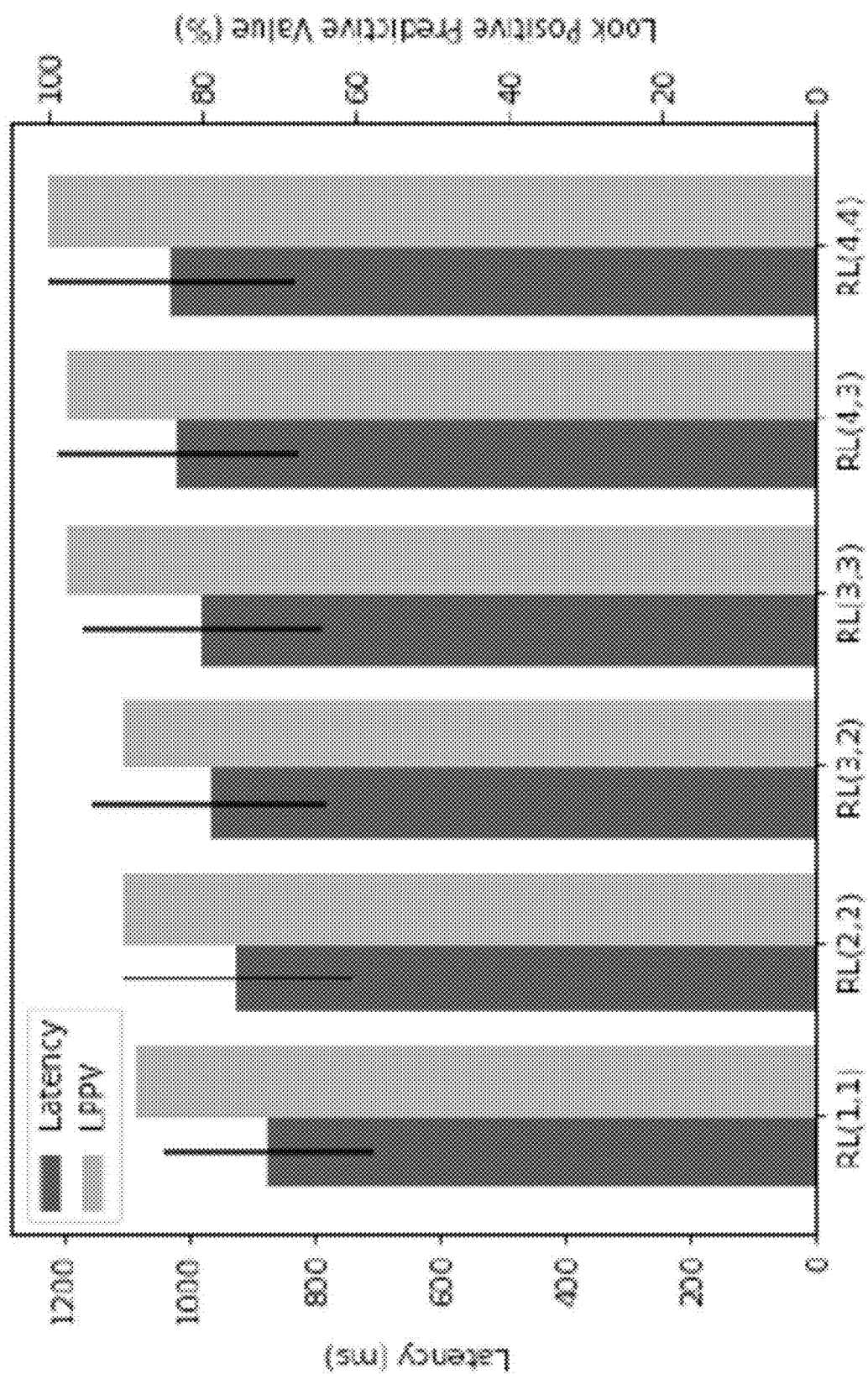
FIG. 7 illustrates an example graph comparing look positive predictive values and latencies, in accordance with one embodiment of the present disclosure.

FIG. 7 illustrates an example graph comparing look positive predictive values and latencies, in accordance with one embodiment of the present disclosure. As illustrated, latency and LPPV increases from RL(1,1) to RL(4,4). The rate of increasing latency and LPPV may taper off around RL(4,3) for latency and RL(3,3,) for LPPV.

Figure 8:
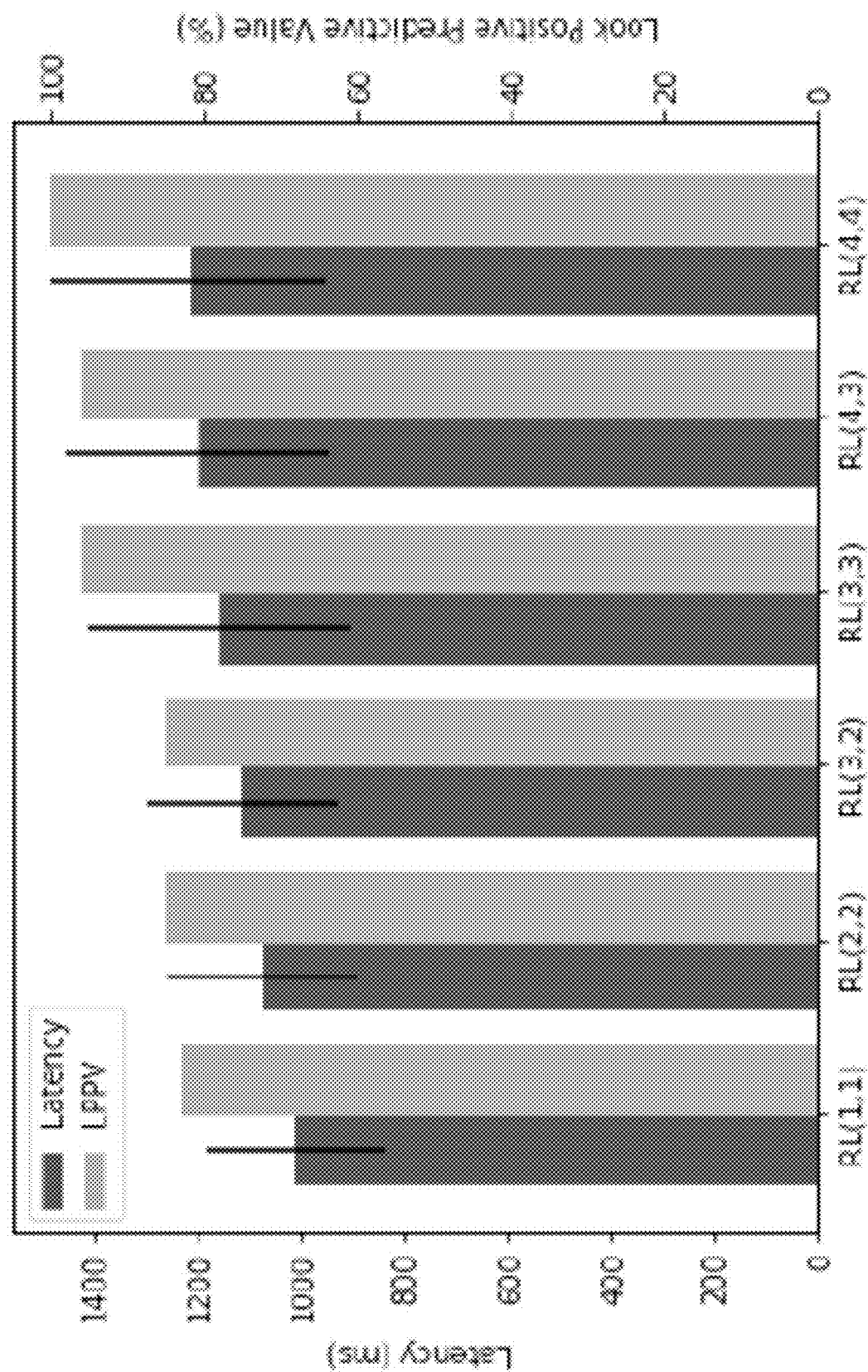
FIG. 8 illustrates an example graph comparing look positive predictive values and latencies, in accordance with one embodiment of the present disclosure.

FIG. 8 illustrates an example graph comparing look positive predictive values and latencies, in accordance with one embodiment of the present disclosure. As illustrated, latency and LPPV increases from RL(1,1) to RL(4,4). The rate of increasing latency and LPPV may taper off around RL(4,3) for latency and RL(3,3,) for LPPV.

Figure 9:
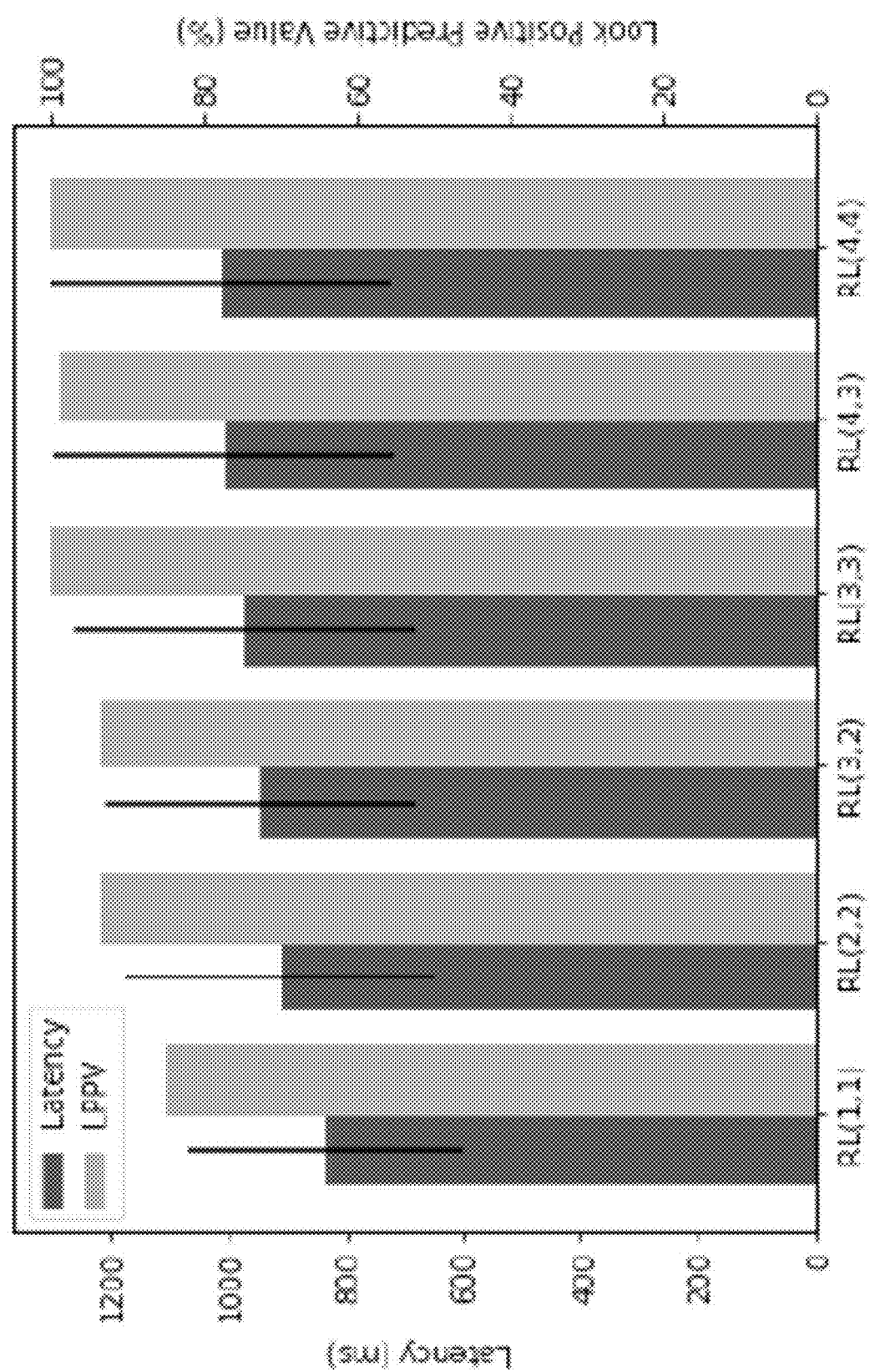
FIG. 9 illustrates an example graph comparing look positive predictive values and latencies, in accordance with one embodiment of the present disclosure.

FIG. 9 illustrates an example graph comparing look positive predictive values and latencies, in accordance with one embodiment of the present disclosure. As illustrated, latency and LPPV increases from RL(1,1) to RL(4,4). The rate of increasing latency and LPPV may taper off around RL(4,3) for latency and RL(3,3,) for LPPV.

Figure 10:
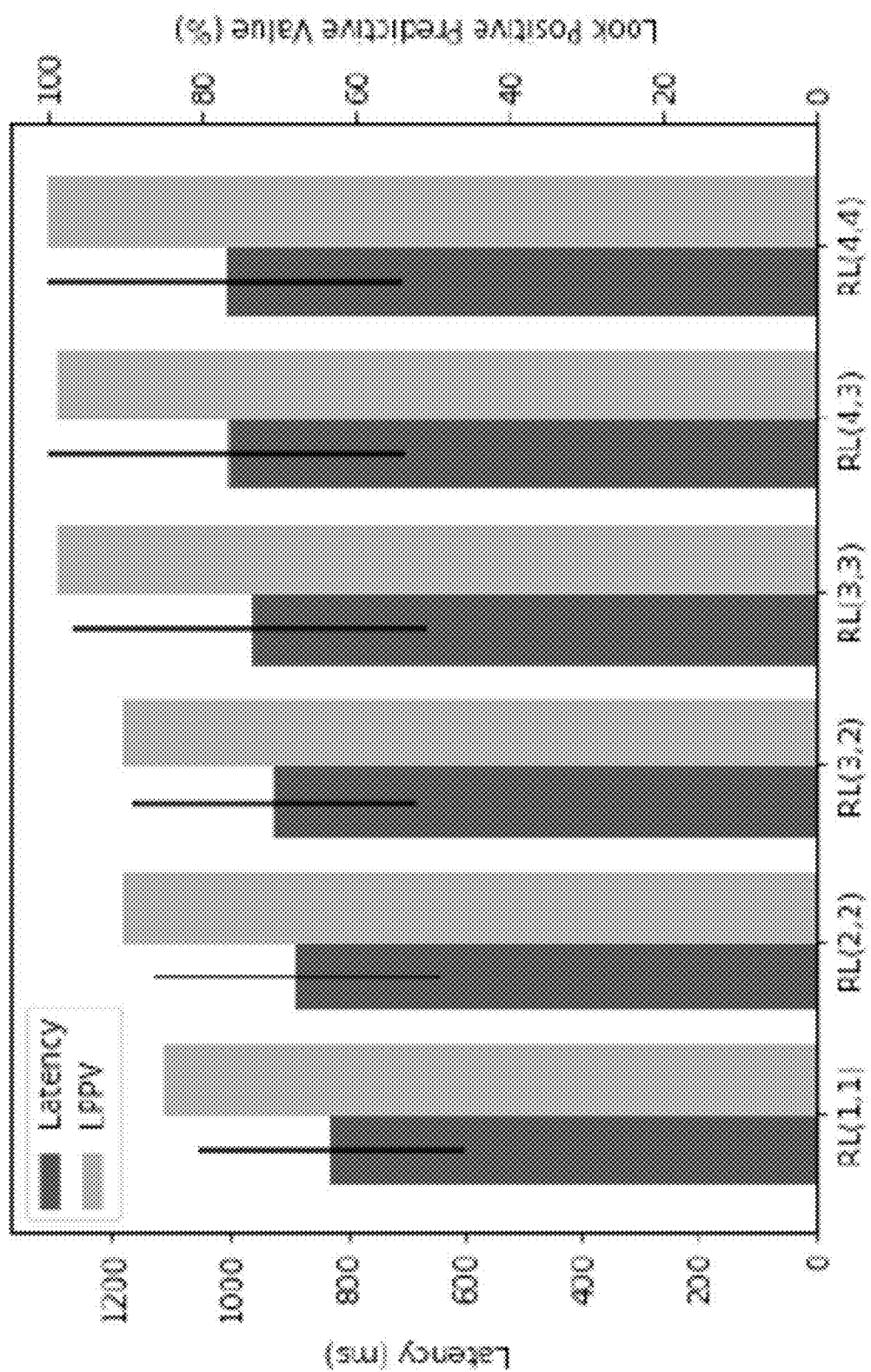
FIG. 10 illustrates an example graph comparing look positive predictive values and latencies, in accordance with one embodiment of the present disclosure.

FIG. 10 illustrates an example graph comparing look positive predictive values and latencies, in accordance with one embodiment of the present disclosure. As illustrated, latency and LPPV increases from RL(1,1) to RL(4,4). The rate of increasing latency and LPPV may taper off around RL(4,3) for latency and RL(3,3,) for LPPV.

Figure 11:
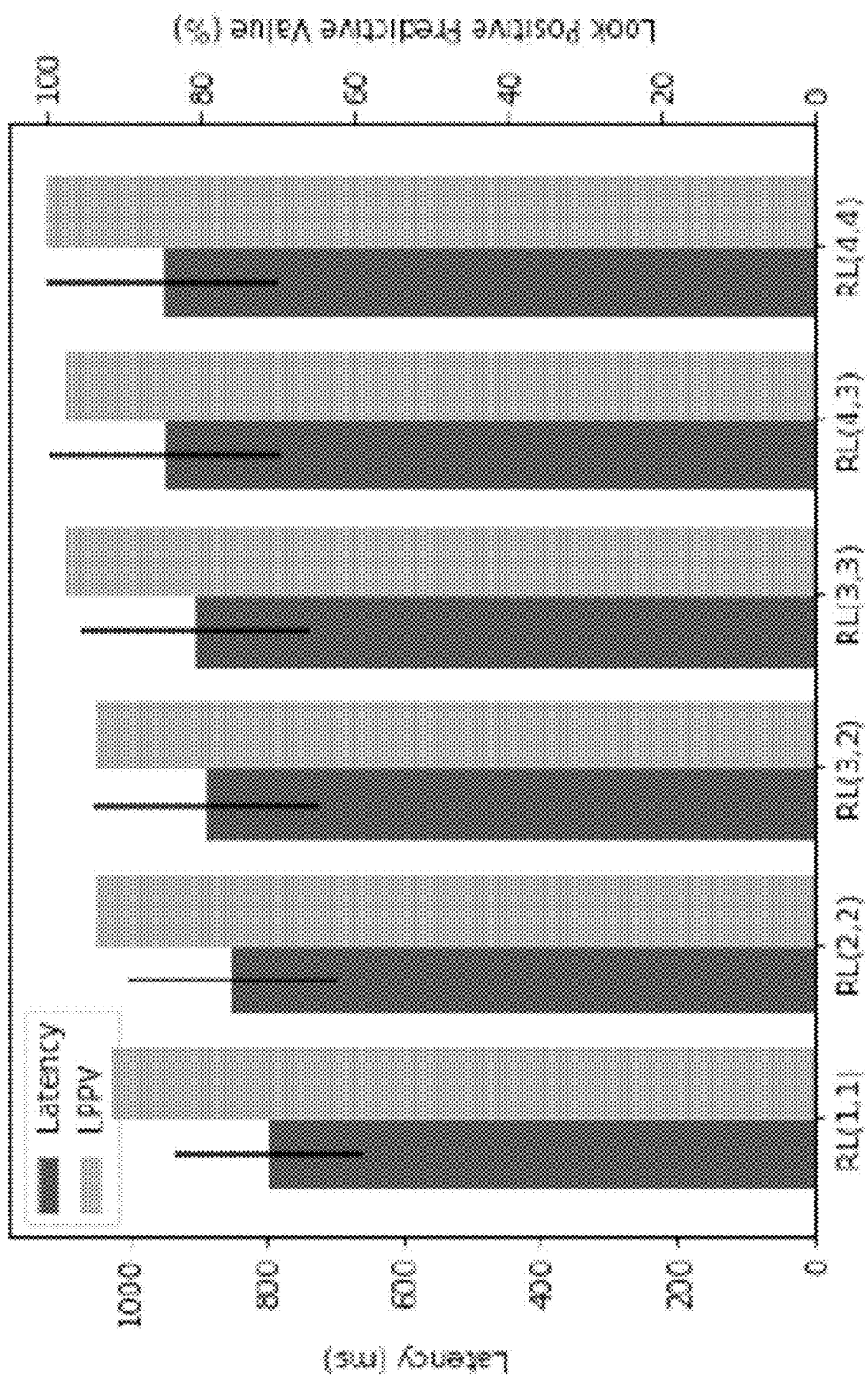
FIG. 11 illustrates an example graph comparing look positive predictive values and latencies, in accordance with one embodiment of the present disclosure.

FIG. 11 illustrates an example graph comparing look positive predictive values and latencies, in accordance with one embodiment of the present disclosure. As illustrated, latency and LPPV increases from RL(1,1) to RL(4,4). The rate of increasing latency and LPPV may taper off around RL(4,3) for latency and RL(3,3,) for LPPV.

While general reference may be made to a joint look at an object, a gaze triad may also be detected, which includes a look to a face before and after a look to an object. In some embodiments, shared eye gaze may also be detected. In embodiments, the movement of every gaze dot may be tracked relative to the object bounding boxes across frames to speed up the look detection process. For some of these additional examples, face detection network may be added.

Figure 12:
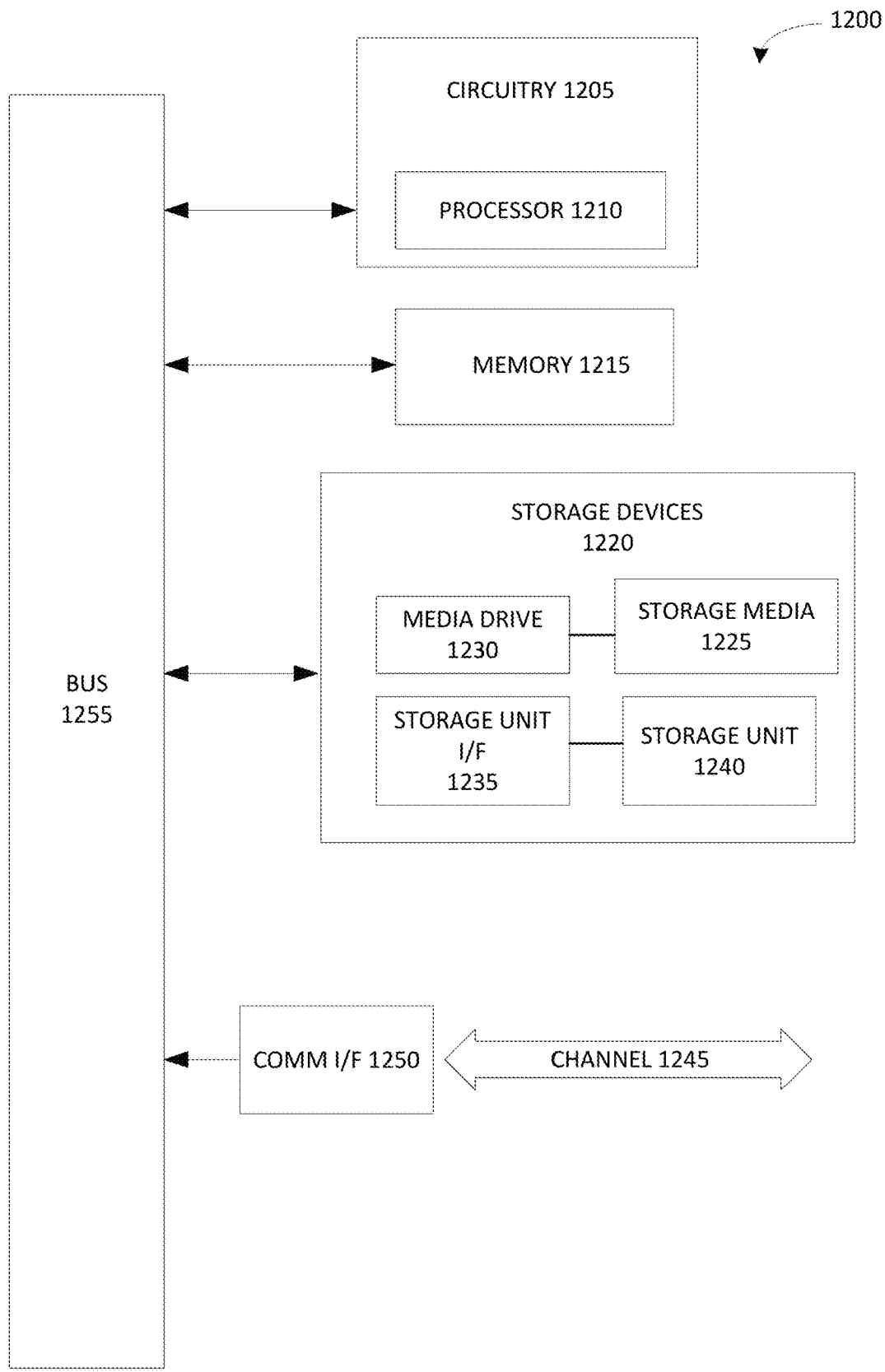
FIG. 12 illustrates an example computing component that may be used to implement features of various embodiments of the disclosure The figures are not intended to be exhaustive or to limit the invention to the precise form disclosed. It should be understood that the invention can be practiced with modification and alteration, and that the disclosed technology be limited only by the claims and the equivalents thereof.

FIG. 12 illustrates example computing component 1200, which may in some instances include a processor on a computer system (e.g., control circuit). Computing component 1200 may be used to implement various features and/or functionality of embodiments of the systems, devices, and methods disclosed herein. With regard to the above-described embodiments set forth herein in the context of systems, devices, and methods described with reference to FIGS. 1-11, including embodiments involving the control circuit, one of skill in the art will appreciate additional variations and details regarding the functionality of these embodiments that may be carried out by computing component 1200. In this connection, it will also be appreciated by one of skill in the art upon studying the present disclosure that features and aspects of the various embodiments (e.g., systems) described herein may be implemented with respected to other embodiments (e.g., methods) described herein without departing from the spirit of the disclosure.

As used herein, the term component may describe a given unit of functionality that may be performed in accordance with one or more embodiments of the present application. As used herein, a component may be implemented utilizing any form of hardware, software, or a combination thereof. For example, one or more processors, controllers, ASICs, PLAs, PALs, CPLDs, FPGAs, logical components, software routines, or other mechanisms may be implemented to make up a component. In implementation, the various components described herein may be implemented as discrete components or the functions and features described may be shared in part or in total among one or more components. In other words, as would be apparent to one of ordinary skill in the art after reading this description, the various features and functionality described herein may be implemented in any given application and may be implemented in one or more separate or shared components in various combinations and permutations. Even though various features or elements of functionality may be individually described or claimed as separate components, one of ordinary skill in the art will understand upon studying the present disclosure that these features and functionality may be shared among one or more common software and hardware elements, and such description shall not require or imply that separate hardware or software components are used to implement such features or functionality.

Where components or components of the application are implemented in whole or in part using software, in embodiments, these software elements may be implemented to operate with a computing or processing component capable of carrying out the functionality described with respect thereto. One such example computing component is shown in FIG. 12. Various embodiments are described in terms of example computing component 1200. After reading this description, it will become apparent to a person skilled in the relevant art how to implement example configurations described herein using other computing components or architectures.

Referring now to FIG. 12, computing component 1200 may represent, for example, computing or processing capabilities found within mainframes, supercomputers, workstations or servers; desktop, laptop, notebook, or tablet computers; hand-held computing devices (tablets, PDA's, smartphones, cell phones, palmtops, etc.); or the like, depending on the application and/or environment for which computing component 1200 is specifically purposed.

Computing component 1200 may include, for example, one or more processors, controllers, control components, or other processing devices, such as a processor 1210, and such as may be included in 1205. Processor 1210 may be implemented using a special-purpose processing engine such as, for example, a microprocessor, controller, or other control logic. In the illustrated example, processor 1210 is connected to bus 1255 by way of 1205, although any communication medium may be used to facilitate interaction with other components of computing component 1200 or to communicate externally.

Computing component 1200 may also include one or more memory components, simply referred to herein as main memory 1215. For example, random access memory (RAM) or other dynamic memory may be used for storing information and instructions to be executed by processor 1210 or 1205. Main memory 1215 may also be used for storing temporary variables or other intermediate information during execution of instructions to be executed by processor 1210 or 1205. Computing component 1200 may likewise include a read only memory (ROM) or other static storage device coupled to bus 1255 for storing static information and instructions for processor 1210 or 1205.

Computing component 1200 may also include one or more various forms of information storage devices 1220, which may include, for example, media drive 1230 and storage unit interface 1235. Media drive 1230 may include a drive or other mechanism to support fixed or removable storage media 1225. For example, a hard disk drive, a floppy disk drive, a magnetic tape drive, an optical disk drive, a CD or DVD drive (R or RW), or other removable or fixed media drive may be provided. Accordingly, removable storage media 1225 may include, for example, a hard disk, a floppy disk, magnetic tape, cartridge, optical disk, a CD or DVD, or other fixed or removable medium that is read by, written to or accessed by media drive 1230. As these examples illustrate, removable storage media 1225 may include a computer usable storage medium having stored therein computer software or data.

In alternative embodiments, information storage devices 1220 may include other similar instrumentalities for allowing computer programs or other instructions or data to be loaded into computing component 1200. Such instrumentalities may include, for example, fixed or removable storage unit 1240 and storage unit interface 1235. Examples of such removable storage units 1240 and storage unit interfaces 1235 may include a program cartridge and cartridge interface, a removable memory (for example, a flash memory or other removable memory component) and memory slot, a PCMCIA slot and card, and other fixed or removable storage units 1240 and storage unit interfaces 1235 that allow software and data to be transferred from removable storage unit 1240 to computing component 1200.

Computing component 1200 may also include a communications interface 1250. Communications interface 1250 may be used to allow software and data to be transferred between computing component 1200 and external devices. Examples of communications interface 1250 include a modem or soft modem, a network interface (such as an Ethernet, network interface card, WiMedia, IEEE 1212.XX, or other interface), a communications port (such as for example, a USB port, IR port, RS232 port Bluetooth® interface, or other port), or other communications interface. Software and data transferred via communications interface 1250 may typically be carried on signals, which may be electronic, electromagnetic (which includes optical) or other signals capable of being exchanged by a given communications interface 1250. These signals may be provided to/from communications interface 1250 via channel 1245. Channel 1245 may carry signals and may be implemented using a wired or wireless communication medium. Some non-limiting examples of channel 1245 include a phone line, a cellular or other radio link, an RF link, an optical link, a network interface, a local or wide area network, and other wired or wireless communications channels.

In this document, the terms "computer program medium" and "computer usable medium" are used to generally refer to transitory or non-transitory media such as, for example, main memory 1215, storage unit interface 1235, removable storage media 1225, and channel 1245. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions may enable the computing component 1200 or a processor to perform features or functions of the present application as discussed herein.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent component names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "component" does not imply that the components or functionality described or claimed as part of the component are all configured in a common package. Indeed, any or all of the various components of a component, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A computer-implemented method comprising:
    obtaining a first gaze stream, wherein the first gaze stream comprises first gaze location data that identifies where a first pupil of a first participant is looking in a real-world environment as a function of time and a first gaze confidence score specifying an accuracy of the first gaze location data;
    obtaining a second gaze stream, wherein the second gaze stream comprises second gaze location data that identifies where a second pupil of the first participant is looking in the real-world environment as a function of time and a second gaze confidence score specifying an accuracy of the second gaze location data;
    based on the first and second gaze confidence scores, rectifying the first and second gaze location data into a first rectified gaze stream that identifies where the first participant is looking in the real-world environment as a function of time;
    obtaining a third gaze stream, wherein the third gaze stream comprises third gaze location data that identifies where a first pupil of a second participant is looking in the real-world environment as a function of time and a third gaze confidence score specifying an accuracy of the third gaze location data;
    obtaining a fourth gaze stream, wherein the fourth gaze stream comprises fourth gaze location data that identifies where a second pupil of the second participant is looking in the real-world environment as a function of time and a fourth gaze confidence score specifying an accuracy of the fourth gaze location data;
    based on the third and fourth gaze confidence scores, rectifying the third and fourth gaze location data into a second rectified gaze stream that identifies where the second participant is looking in the real-world environment as a function of time;
    providing a cue to the first and second participants to view an object in the real-world environment;
    detecting joint attention between the first participant and the second participant based on the rectified first and second gaze streams indicating that both the first participant and the second participant are focusing on the object over a threshold time interval within a time window of predetermined length; and
    providing feedback based on detecting the joint attention.

2. The computer-implemented method of claim 1, further comprising filtering the first gaze location data based on a Kalman filter and the first gaze confidence score.

3. The computer-implemented method of claim 1, further comprising:
    generating a visualization of a bounding box surrounding the object; and
    displaying the visualization on a head-mounted display when the object is in a current frame of a video stream of the real-world environment from a perspective of the first participant.

4. The computer-implemented method of claim 1, further comprising:
    detecting the object in a current frame of a video stream of the real-world environment from a perspective of the first participant using a convolutional neural network;
    generating a visualization of a bounding box surrounding the object in the current frame; and
    displaying the visualization on a head-mounted display when the object is in the current frame.

5. The computer-implemented method of claim 1, wherein the cue comprises one of an audio cue and a visual cue.

6. The computer-implemented method of claim 1, wherein the feedback comprises one of an audio cue and a visual cue.

7. A system comprising:
    one or more processors; and
    non-transitory storage medium coupled to the one or more processors to store instructions, which when executed by the one or more processors, cause the system to:
        obtain a first gaze stream, wherein the first gaze stream comprises first gaze location data that identifies where a first pupil of a first participant is looking in a real-world environment as a function of time and a first gaze confidence score specifying an accuracy of the first gaze location data;
obtaining a second gaze stream, wherein the second gaze stream comprises second gaze location data that identifies where a second pupil of the first participant is looking in the real-world environment as a function of time and a second gaze confidence score specifying an accuracy of the second gaze location data;
based on the first and second gaze confidence scores, rectify the first and second gaze location data into a first rectified gaze stream that identifies where the first participant is looking in the real-world environment as a function of time;
obtain a third gaze stream, wherein the third gaze stream comprises third gaze location data that identifies where a first pupil of a second participant is looking in the real- world environment as a function of time and a third gaze confidence score specifying an accuracy of the third gaze location data;
obtain a fourth gaze stream, wherein the fourth gaze stream comprises fourth gaze location data that identifies where a second pupil of the second participant is looking in the real-world environment as a function of time and a fourth gaze confidence score specifying an accuracy of the fourth gaze location data;
based on the third and fourth gaze confidence scores, rectify the third and fourth gaze location data into a second rectified gaze stream that identifies where the second participant is looking in the real-world environment as a function of time;
provide a cue to the first and second participants to view an object in the real-world environment;
detect joint attention between the first participant and the second participant based on the rectified first and second gaze streams indicating that both the first participant and the second participant are focusing on the object over a threshold time interval within a time window of predetermined length; and
provide feedback based on detecting the joint attention.

8. The system of claim 7, wherein the non-transitory storage medium is coupled to the one or more processors to store additional instructions, which when executed by the one or more processors, further cause the system to:
filter the first gaze location data based on a Kalman filter and the first gaze confidence score; and
filter the second gaze location data based on a Kalman filter and the second gaze confidence score.

9. The system of claim 7, wherein the non-transitory storage medium is coupled to the one or more processors to store additional instructions, which when executed by the one or more processors, further cause the system to:
generate a visualization of a bounding box surrounding the object; and
display the visualization on a see-through display when the object is in a current frame of a video stream of the real-world environment from a perspective of the first participant.

10. The system of claim 7, wherein the non-transitory storage medium is coupled to the one or more processors to store additional instructions, which when executed by the one or more processors, further cause the system to:
detect the object in a current frame of a video stream of the real-world environment from a perspective of the first participant using a convolutional neural network;
generate a visualization of a bounding box surrounding the object in the current frame; and
display the visualization on a see-through display when the object is in the current frame.

11. The system of claim 7, wherein the non-transitory storage medium is coupled to the one or more processors to store additional instructions, which when executed by the one or more processors, cause the system to detect a gaze triad from at least one participant of the first and second participant, wherein the gaze triad comprises a look to a face before and after a look to the object.

12. The system of claim 7, wherein detecting the joint attention comprises applying a runlength filter, wherein the runlength filter comprises a window size parameter specifying a number of frames to consider together and a hit threshold specifying a minimum number of hits in the number of frames to be identified as a gaze.

13. A computer-implemented method comprising:
obtaining a first video stream comprising a video of a real-world environment from a perspective of a first participant;
obtaining a second video stream comprising a video of a real-world environment from a perspective of a second participant;
a first gaze stream, wherein the first gaze stream comprises first gaze location data that identifies where a first pupil of the first participant is looking in a real-world environment as a function of time and a first gaze confidence score specifying an accuracy of the first gaze location data;
obtaining a second gaze stream, wherein the second gaze stream comprises second gaze location data that identifies where a second pupil of the first participant is looking in the real-world environment as a function of time and a second gaze confidence score specifying an accuracy of the second gaze location data;
based on the first and second gaze confidence scores, rectifying the first and second gaze location data into a first rectified gaze stream that identifies where the first participant is looking in the real-world environment as a function of time;
obtaining a third gaze stream, wherein the third gaze stream comprises third gaze location data that identifies where a first pupil of the second participant is looking in the real-world environment as a function of time and a third gaze confidence score specifying an accuracy of the third gaze location data;
obtaining a fourth gaze stream, wherein the fourth gaze stream comprises fourth gaze location data that identifies where a second pupil of the second participant is looking in the real-world environment as a function of time and a fourth gaze confidence score specifying an accuracy of the fourth gaze location data;
based on the third and fourth gaze confidence scores, rectifying the third and fourth gaze location data into a second rectified gaze stream that identifies where the second participant is looking in the real-world environment as a function of time;
providing a cue to the first and second participants to view an object in the real-world environment;
detecting joint attention between the first participant and the second participant based on the rectified first and second gaze streams indicating that both the first participant and the second participant are focusing on the object over a threshold time interval within a time window of predetermined length; and
providing feedback based on detecting the joint attention.

14. The computer-implemented method of claim 13, further comprising:
  generating a bounding box surrounding the object;
  displaying the bounding box via a first see-through display when the object is in a current frame of the first video stream; and
  displaying the bounding box via a second see-through display when the object is in a current frame of the second video stream.

15. The computer-implemented method of claim 14, wherein displaying the bounding box via the first see-through display when the object is in the current frame of the first video stream comprises changing a size of the bounding box based on at least one of:
  a current size of the bounding box;
  the first gaze confidence score; and
  a depth of the object from the first participant.

16. The computer-implemented method of claim 13, further comprising detecting a gaze triad, wherein the gaze triad comprises a look to a face before and after a look to the object.

17. The computer-implemented method of claim 13, further comprising filtering the first gaze location data based on a Kalman filter and the first gaze confidence score.

\* \* \* \* \*